United States Patent
Gotor et al.

(10) Patent No.: US 11,561,175 B2
(45) Date of Patent: Jan. 24, 2023

(54) DETECTION OF HYDROCARBON CONTAMINATION IN SOIL AND WATER

(71) Applicant: Bundesrepublik Deutschland, vertreten durch die Bundesministerin für Wirtschaft und Energie, Berlin (DE)

(72) Inventors: Raúl Gotor, Berlin (DE); Jérémy Bell, Berlin (DE); Knut Rurack, Berlin (DE)

(73) Assignee: Bundesrepublik Deutschland, vertreten durch die Bundesministerin für Wirtschaft und Energie, diese vertreten durch den Präsidenten der Bundesanstalt für Materialforgchung und- Prüfung (BAM), Berlin (DE)

(*) Notice: Subject to any disclaimer, the term of this patent is extended or adjusted under 35 U.S.C. 154(b) by 224 days.

(21) Appl. No.: 16/650,426

(22) PCT Filed: Sep. 29, 2017

(86) PCT No.: PCT/EP2017/074876
§ 371 (c)(1),
(2) Date: Mar. 25, 2020

(87) PCT Pub. No.: WO2019/063100
PCT Pub. Date: Apr. 4, 2019

(65) Prior Publication Data
US 2020/0232918 A1    Jul. 23, 2020

(51) Int. Cl.
*G01N 21/64* (2006.01)
*G01N 33/24* (2006.01)
(Continued)

(52) U.S. Cl.
CPC ............. *G01N 21/64* (2013.01); *G01N 21/76* (2013.01); *G01N 31/22* (2013.01); *G01N 33/1833* (2013.01); *G01N 33/241* (2013.01)

(58) Field of Classification Search
CPC ........ G01N 21/64; G01N 21/76; G01N 31/22; G01N 33/1833; G01N 33/241
See application file for complete search history.

(56) References Cited

U.S. PATENT DOCUMENTS 5,691,148 A    11/1997    Allen
2004/0241877 A1    12/2004    Price et al.
(Continued)

FOREIGN PATENT DOCUMENTS

DE    4314198 A1    11/1994
EP    3688457 A1    8/2020
(Continued)

OTHER PUBLICATIONS

Solvatochromic and Fluorogenic Dyes ans Environment-Sensitive Probes: Design and Biological Applications Andrey S. Klymchenko Acc. Chem. Res. 2017, 50, 366-375 (Year: 2017).*
(Continued)

*Primary Examiner* — Brian R Gordon
*Assistant Examiner* — Dwan A Gerido
(74) *Attorney, Agent, or Firm* — Bachman & LaPointe, P.C.

(57) ABSTRACT

A method for the detection of hydrocarbon contamination in a sample is disclosed. The method includes contacting a sample with a molecular probe. The molecular probe has a photoluminescence which is environmentally sensitive. The photoluminescence from the molecular probe is collected. The method includes determining whether the photoluminescence is indicative of a hydrocarbon contaminated sample. A test strip for the detection of hydrocarbon contamination in a sample is also disclosed. The test strip includes a molecular probe embedded in a substrate and/or immobilized to the substrate, the molecular probe having a
(Continued)

photoluminescence which is environmentally sensitive to hydrocarbon contaminated sample.

12 Claims, 11 Drawing Sheets

(51) Int. Cl.
  *G01N 33/18* (2006.01)
  *G01N 21/76* (2006.01)
  *G01N 31/22* (2006.01)

(56) References Cited

U.S. PATENT DOCUMENTS

| | | | |
|---|---|---|---|
| 2011/0151576 | A1 | 6/2011 | Perfect et al. |
| 2020/0232918 | A1 | 7/2020 | Bell et al. |

FOREIGN PATENT DOCUMENTS

| | | | |
|---|---|---|---|
| GB | 2529719 | A | 3/2016 |
| WO | 8809798 | A1 | 12/1988 |
| WO | WO 88/09798 | * | 12/1988 |
| WO | 9743636 | A1 | 11/1997 |
| WO | 2014069897 | A1 | 5/2014 |
| WO | 2019063100 | A1 | 8/2020 |

OTHER PUBLICATIONS

C. Peinado et al, "Solvatochromic and rigidochromic fluorescent probes based on D-π-A diaryl ethylene and butadiene derivatives for UV-curing monitoring", Polymer, vol. 42, pp. 2815-2825.
Zeng Ziqiang et al, edited, "Natural Gas Gathering and Transmission Project", China Petroleum Industry Press.
Hesam Shahin et al, "Mobile phone as a fluorescence reader", Optica. Applicata, vol. 43, No. 3, pp. 413-420.
Chinese office action for patent application No. 201780095367.8 dated Jan. 29, 2022.
Canadian office action for patent application No. 3,074,622 dated Apr. 28, 2021.
Brazilian office action for patent application No. BR112020005018-0 dated Aug. 3, 2021.
Virta et al., "A Luminescence-Based Mercury Biosensor", Analytical Chemistry, vol. 67, No. 3, Feb. 1, 1995., pp. 367-669.
International search report for patent application No. PCT/EP2017/074876 dated Mar. 7, 2018.
Canadian office action for patent application No. CA 3,074,622 dated Nov. 10, 2021.
Indian office action for patent application No. 202017007780 dated Feb. 7, 2020.
Kenji Hanabusa et al., Fluorescent Gelators for Detection of Explosives, Bulletin of the Chemical Society of Japan, 2016, vol. 89, No. 11, 1391-1401, doi.org/10.1246/bcsj.20160232.
Ang-yang Yu and Jing Y, Computational Investigations about the Ground and Excited States' Properties of Trans-4-N, N-Dimethylamino-4'-Nitro-Stilbene (DNS) and Trans-4-N,N-Dimethyl-Amino-4'-Cyanostilbene (DCS) Derivatives, Journal of Theoretical & Computational Science, 2015, 2:3.
Hesam Shahin, Ratal Walczak, Mobile phone as a fluorescence reader, Optica Applicata, vol. XLIII, No. 3, 2013, DOI: 10.5277/oa130301.
Megyesi, Monika & Biczók, László & Miskolczy, Zsombor. (2010). Effects of solvent polarity and hydrogen bonding on the fluorescence properties of trans-4-hydroxy-4 '-nitrostilbenes. Chemical Physics Letters. 489. 59-63. 10.1016/j.cplett.2010.02.050.
Lin CK, Wang YF, Cheng YC, Yang JS. Multisite constrained model of trans-4-(N,N-dimethylamino)-4'-nitrostilbene for structural elucidation of radiative and nonradiative excited states. J Phys Chem A. Apr. 18, 2013;117(15):3158-64. doi: 10.1021/jp310770s. Epub Apr. 5, 2013. PMID: 23514591.
Dong, Jinqiao & Tummanapelli, Anil & Li, Xu & Ying, Shaoming & Hirao, Hajime & Zhao, Dan. (2016). Fluorescent Porous Organic Frameworks Containing Molecular Rotors for Size-Selective Recognition. Chemistry of Materials. 28. 10.1021 /acs.chemmater.6b03376.
Alamiry, Mohammed & Benniston, Andrew & Copley, Graeme & Elliott, Kristopher & Harriman, Anthony & Stewart, Beverly & Zhi, Yong-Gang. (2008). A Molecular Rotor Based on an Unhindered Boron Dipyrromethene (Bodipy) Dye. Chem. Mat.. 20. 10.1021/cm800702c.
Giseop Kwak et al., Fluorescent Viscosity Sensor Film of Molecular-Scale Porous Polymer with Intramolecular π-Stack Structure, Macromolecules, 2011, 44, 432-436, DOI: 10.1021/ma102798j.
Zhang, Yuping and Liang, Chunshuang and Jiang, Shimei, A solvatochromic cyanostilbene derivative as an intensity and wavelength-based fluorescent sensor for water in organic solvents, New J. Chem., 2017,41, 8644-8649. http://dx.doi.org/10.1039/C7NJ01361B.
Park et al. An immunoblot-based optical biosensor for screening of osteoarthritis using a smartphone-embedded illuminometer, Anal. Methods, 2015,7, 6437-6442, https://doi.org/10.1039/C5AY01198A.
Wei et al. Fluorescent Imaging of Single Nanoparticles and Viruses on a Smart Phone, ACS Nano 2013, 7, 10, 9147-9155, Sep. 9, 2013 https://doi.org/10.1021/nn4037706.
Canadian Office Action for Patent Application No. 3,074,622 dated Jun. 10, 2022.
Castro Ana M. et al: "Hydrocarbon in water sensing with PTFE membranes doped with a luminescent Ru(ii) poly(pyridyl) complex", Journal of Materials Chemistry, vol. 15, No. 27-28, Jan. 1, 2005, p. 2952, XP055945499, GB ISSN: 0959-9428, DOI: 10.1039/b501785h Retrieved from the Internet: URL:https://pubs.rsc.org/En/content/articlepdf/2005/jm/b501785h.
Ibañez Gabriela A. et al: "Luminescence Sensors Applied to Water Analysis of Organic Pollutants—An Update", Sensors, vol. 11, No. 12, Jan. 1, 2011, pp. 11081-11102, XP055945459, DOI: 10.3390/s111211081, Retrieved from the Internet: URL:https://www.ncbi.nlm.nih.gov/pmc/articles/PMC3251971/pdf/ sensors-11-11081.pdf.
G. Corradini Maria et al: "Identifying and selecting edible luminescent probes as sensors of food quality",AIMS Biophysics,vol. 3, No. 2, Jan. 1, 2016, pp. 319-339, XP055945456, ISSN: 2377-9098, DOI: 10.3934/biophy.2016.2.319.
European Office Action for Patent Application No. 17780067.9 dated Jul. 28, 2022.
Chinese office action dated Nov. 3, 2022 for corresponding application No. 201780095367.8.

* cited by examiner

DETECTION OF HYDROCARBON CONTAMINATION IN SOIL AND WATER

FIELD AND BACKGROUND

The present disclosure is in regard to the detection of hydrocarbon contamination in a sample such as soil or water.

Contamination of oceans, rivers and lakes with hydrocarbons such as oil and greases (e.g. petrol, fuel, and other hydrocarbon derivatives) is a common problem around the world. Contaminated waters lead to environmental degradation and strong risks in human and aquatic health. Regulatory agencies may have limits for total oil and greases (TOG) or total petroleum hydrocarbon (TPH) in water, implying strong interests for industries to be able to determine TOG and TPH in water to be sure they meet the limits.

Additionally, non-profit environmental organizations which are constantly mapping different areas to find possible illegal spills, are in the need of improvements in technology to measure these values. The possibility of in-field measurements is highly desired as well, as water streams produced in some industries or samples at locations that are difficult to reach need to be constantly monitored, while normal laboratory analysis would be too time-consuming and costly.

Normally, the TOG content in water is determined by extraction from water into a non-polar solvent, concentration, and posterior analysis using different methods. Among these methods, most commonly used are gravimetric analysis (EPA 1664), gas chromatography-flame ionization detection, (ISO 9377-2), UV-fluorescence, quantum Cascade laser infrared spectrometry (QCL-IR), non-dispersive/fixed filter IR analyzer. Unfortunately, these methods have some drawbacks such as high costs, requiring instrumentation that is difficult to transport, and needing highly trained personal. With some methods, cyclic hydrocarbons escape detection and/or the method is sensitive only to polycyclic aromatic hydrocarbons. Some methods use atmospheric ozone depleting chemicals, many now banned by the Montreal Protocol.

It is desirable to have a way to determine rapidly if a water or soil sample is contaminated, qualitatively or quantitatively. It is also desirable for it to be possibly done by untrained personnel. Laboratory methods and more complex field methods usually require a certain degree of expertise in dealing with the device, possible sample preparation steps as well as the interpretation of the results, and are therefore reserved for professionals. It is also desirable that the costs are low.

SUMMARY

In view of the above, disclosed herein is a test strip which can be, for example, immersed in water and/or dragged over soil and read out with a hand-held reader (e.g. a mobile communication device or smartphone or tablet), which then can possibly output a determination of whether the sample is contaminated with hydrocarbon(s).

Disclosed herein is a method for detection of hydrocarbon contamination in a sample, making use of a molecular probe which has an environmentally sensitive photoluminescence. In some embodiments, the probe is immobilized to a test strip. Disclosed herein is a method and a test strip. Further configurations, details, and features of the present invention are also described herein. The disclosed method can provide a rapid, portable, and inexpensive analysis that does not require extensive training to perform.

Disclosed herein is a system, which may use photoluminescence from environmentally sensitive molecular probes to overcome many of the above-mentioned problems. Concentration of hydrocarbon such as oil and grease in water may be determined quickly in the field, with the use of inexpensive technology (e.g. fluorescence or smartphone reader, or tablet reader) in both a qualitative (e.g. quickly dipping a test strip in water and measuring it afterwards, without oil and grease extraction) and/or quantitative fashion (assisted with solvents).

Herein is disclosed a method for the detection of hydrocarbon contamination in a sample, such as water, soil, or extract thereof, the method comprising: contacting a sample with a molecular probe, the molecular probe having a photoluminescence which is environmentally sensitive; collecting the photoluminescence from the molecular probe; and determining whether the photoluminescence is indicative of a hydrocarbon contaminated sample.

According to a further embodiment, which can be combined with any other embodiment disclosed herein, the molecular probe is environmentally sensitive to viscosity and/or polarity. A molecular probe that is particularly sensitive to viscosity and/or polarity is advantageous because the presence of hydrocarbons can significantly impact viscosity and polarity.

According to a further embodiment, which can be combined with any other embodiment disclosed herein, the molecular probe has a twisted intramolecular charge transfer state, the twisted intramolecular charge transfer state inducing less photoluminescence than another state, such as a planar state. The twisted intramolecular charge transfer state may be variably accessible. The reduced photoluminescence may translate as being less luminescent, having a shorter lifetime, having a lower photoluminescence quantum yield, etc.

The twisted intramolecular charge transfer state may be variably accessible, such as being dependent on environmental conditions such as viscosity and/or polarity. A probe with a twisted intramolecular charge transfer state can be advantageous because such states can be variably accessible depending on the environment of the molecular probe, and/or such states can undergo environmentally sensitive processes. The environmental sensitivity of the molecular probe can affect the photoluminescence of the molecular probe, so that the photoluminescence can be used to determine if the sample is indicative of hydrocarbon contaminated water. Without being bound by theory, a charge transfer state can be particularly sensitive to environmental polarity.

According to a further embodiment, which can be combined with any other embodiment disclosed herein, the molecular probe is a molecular rotor. A molecular probe which is a molecular rotor can be particularly environmentally sensitive, such as to viscosity of the sample.

According to a further embodiment, which can be combined with any other embodiment disclosed herein, the molecular probe comprises a 4-nitrostilbene moiety, such as according to the formula

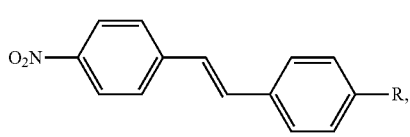

wherein R is selected from

referred to as 4-DNS,

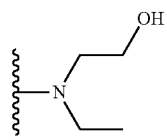

referred to as 4-DNS-OH, and an —N—R'R" moiety functionalized with a member selected from the group of: an alkyl, an alkenyl, an alkynyl, an alkyl halides, a thioalkyl, a hydroxyalkyl, an alkyl phosphate, an alkyl phosphoric, an alkyl boronate, an alkyl boronic, a carboxylic acid, a carboxylate, a sulfonic acid, a sulfonate, a silano, and combinations thereof.

Using a 4-nitrostilbene moiety, such as those mentioned above, can be advantageous because they can provide an environmentally sensitive photoluminescence. The 4-nitrostilbene based species can be used for the detection of hydrocarbons in a sample.

According to a further embodiment, which can be combined with any other embodiment disclosed herein, the molecular probe is solvatochromic and/or solvatokinetic. A solvatochromic and/or solvatokinetic molecular probe can be particularly sensitive to the environment so as to change photoluminescent properties upon exposure to hydrocarbons.

According to a further embodiment, which can be combined with any other embodiment disclosed herein, the molecular probe is immobilized on a hydrophobic substrate, such as a polyvinylidene fluoride substrate. An immobilized form of the molecular probe is useful to provide for a portable format for performing the method which does not require much user training. Polyvinylidene fluoride can possibly aid in maintaining the molecular probe's environmental sensitivity to a liquid sample.

According to a further embodiment, which can be combined with any other embodiment disclosed herein, the sample is water, soil, or an extract thereof. It is desirable to detect the contamination of water and soil with hydrocarbons.

According to a further embodiment, which can be combined with any other embodiment disclosed herein, the method includes estimating a hydrocarbon content of the sample based on the photoluminescence. Such estimation can provide a user with more specific information to determine whether the sample is suitable for certain purposes such as drinking, cooking, and bathing.

According to a further embodiment, which can be combined with any other embodiment disclosed herein, the sample is contacted to the molecular probe by dipping the substrate into the sample or dropping the sample onto the substrate or spraying the substrate with the sample. Wiping and swabbing are also possible. Dipping, dropping, wiping, swabbing, or spraying can be advantageous in that they lead to adequate contact of the molecular probe and the sample, and can be performed by users without extensive training. Alternatively/additionally, the molecular probe can be contacted to the sample by floating a substrate including the immobilized molecular probe on a sample, such floating possibly providing contact between the molecular probe and an extracted hydrocarbon contaminant in an extract/solvent layer at the top of an aqueous sample.

According to a further embodiment, which can be combined with any other embodiment disclosed herein, the method includes determining a signal, a brightness, a brightness ratio (such as taken at two wavelengths), a luminance, a photoluminescence quantum yield, a spectrum, and/or a photoluminescence kinetics such as a lifetime of the photoluminescence; the determination being of the molecular probe in contact or after contact with the sample. The use of different determinations, e.g. photoluminescent signal types and the like, can provide greater sensitivity.

According to a further embodiment, which can be combined with any other embodiment disclosed herein, a portable device such as a smartphone, digital camera, tablet, or mobile communication and computing device, collects the photoluminescence and determines whether the photoluminescence is indicative of the hydrocarbon contamination; the portable device comprising optionally a lens and/or a fiberoptic for collecting the photoluminescence. The use of a portable device can advantageous for allowing the method to be performed in remote areas. A lens and/or fiberoptic can be advantageous for conveniently allowing the photoluminescence to be collected.

According to a further embodiment, which can be combined with any other embodiment disclosed herein, the method also includes exciting the molecular probe with an ultraviolet or visible light source such as a camera flash, a LED, a laser, or an incandescent light. Exciting the molecular probe with such means is advantageous in that it provides a way to generate the photoluminescence.

According to a further embodiment, which can be combined with any other embodiment disclosed herein, the method also includes comparing the photoluminescence to a calibration; such as comparing a signal, such as the luminescence, to a reference (a reference being for example stored data or a reference spot on the test strip). It can be advantageous to have a comparison so as to account for and possibly correct molecular probe photoluminescence variation that may not be directly caused by hydrocarbons.

Herein is disclosed a test strip for the detection of hydrocarbon contamination in a sample, including a molecular probe embedded in a substrate and/or immobilized to the substrate, the molecular probe having a photoluminescence which is environmentally sensitive to hydrocarbon contaminated sample. The test strip can be advantageous for being portable, inexpensive, and easily used.

According to a further embodiment (of the test strip), which can be combined with any other embodiment disclosed herein, the molecular probe is environmentally sensitive to viscosity and/or polarity. A molecular probe that is particularly sensitive to viscosity and/or polarity is advantageous because these properties can be impacted by the presence of hydrocarbons.

According to a further embodiment, which can be combined with any other embodiment disclosed herein, the molecular probe has an accessible twisted intramolecular charge transfer state, the twisted intramolecular charge transfer state inducing less photoluminescence than another state, such as a planar state. A probe with a twisted intramolecular charge transfer state can be advantageous because such states can be variably accessible depending on the environment of the molecular probe, and/or such states can undergo environmentally sensitive processes. The environmental sensitivity of the molecular probe can affect the photoluminescence of the molecular probe, so that the photoluminescence can be used to determine if the sample is indicative of hydrocarbons.

According to a further embodiment, which can be combined with any other embodiment disclosed herein, the molecular probe is a molecular rotor. A molecular probe which is a molecular rotor can be particularly environmentally sensitive, such as to viscosity of the sample.

According to a further embodiment, which can be combined with any other embodiment disclosed herein, the molecular probe comprises a 4-nitrostilbene moiety, such as according to the formula

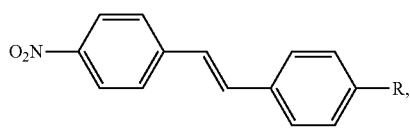

wherein R is selected from

referred to as 4-DNS,

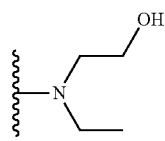

referred to as 4-DNS-OH, and
an —N—R'R" moiety functionalized with a member selected from the group of: an alkyl, an alkenyl, an alkynyl, an alkyl halides, a thioalkyl, a hydroxyalkyl, an alkyl phosphate, an alkyl phosphoric, an alkyl boronate, an alkyl boronic, a carboxylic acid, a carboxylate, a sulfonic acid, a sulfonate, a silano, and combinations thereof.

Using a 4-nitrostilbene moiety, such as those mentioned above, can be advantageous because they can provide an environmentally sensitive photoluminescence. The 4-nitrostilbene based species can be used for the detection of hydrocarbons in a sample.

According to a further embodiment, which can be combined with any other embodiment disclosed herein, the molecular probe is solvatochromic and/or solvatokinetic. A solvatochromic and/or solvatokinetic molecular probe can be particularly sensitive to the environment so as to change photoluminescent properties upon exposure to hydrocarbons.

According to a further embodiment, which can be combined with any other embodiment disclosed herein, the molecular probe is immobilized on a hydrophobic substrate, such as a polyvinylidene fluoride substrate; and/or the molecular probe is embedded in a hydrophobic matrix, such as a polyvinylidene fluoride matrix, on the substrate. An immobilized form of the molecular probe is useful to provide for a portable format for performing the method which does not require much user training. Polyvinylidene fluoride can possibly minimally reduce the molecular probe's environmental sensitivity to a liquid sample.

According to a further embodiment, which can be combined with any other embodiment disclosed herein, the test strip also includes a reference photoluminescent species for comparison to the photoluminescence of the molecular probe; the photoluminescence of the reference species being optionally relatively environmentally insensitive. A reference can provide more information to determine whether the sample is contaminated with hydrocarbons, and may allow for correction of other effects that may influence the photoluminescence.

According to a further embodiment, which can be combined with any other embodiment disclosed herein, the test strip comprises multiple spots and/or lines of photoluminescent species including the molecular probe. Multiple spots can provide for collection of more photoluminescence, possibly allowing for comparison of results, acquisition of more data, and the like, for more robust sampling and more reliable results. According to an additional/alternative embodiment, which can be combined with any other embodiment disclosed herein, the molecular probe is immobilized to a fairly large area of the substrate, such as at least 1 cm$^2$, at least 2 cm$^2$, or at least 4 cm$^2$, and/or more than 90% of the area of the test strip, and/or the entire surface of the substrate and/or test strip. This can be advantageous for providing greater sensitivity, such as an elevated (e.g. brighter) signal, particularly in the presence of a hydrocarbon.

According to a further embodiment, which can be combined with any other embodiment disclosed herein, the test strip is for testing water and/or soil, such as for directly testing a liquid extract thereof. Such detection is advantageous in that it does not require extensive user training or sample work-up.

BRIEF DESCRIPTION OF THE DRAWINGS

FIG. 2 is representative of 4-DNS-OH immobilized on PVDF polymer.

FIG. 6 is illustrative of photoluminescence intensity of 4-DNS-OH adsorbed on PVDF test-strips upon increasing concentration of lubricating oil in cyclohexane.

DETAILED DESCRIPTION

Herein, the terms "microenvironment" and "environment" may be used interchangeably in certain contexts, particularly when referring to the "environment" of a molecular probe. Herein, the terms "dye," and "indicator" may be used, in context, synonymously with "molecular probe" particularly when referring to a nonpolymeric species that has environmentally sensitive photoluminescence. A molecular probe which is grafted to a substrate, as described herein, is to be regarded as a molecular probe. Molecular probes may be grafted, embedded, and/or adsorbed, for example, to polymeric substrates. Herein DNS may be used, in context, synonymously, for 4-DNS. Herein, DNS-OH may be used, in context, synonymously, for 4-DNS-OH.

Herein "photoluminescence" is used as a general term as understood by a skilled person to include fluorescence. Particularly in many of the examples herein, the photoluminescence mechanism is a fluorescence mechanism.

The term TPH herein may refer to total petroleum hydrocarbon; herein the term "PAH" can refer to polycyclic aromatic hydrocarbons; "PH" can refer to petroleum hydrocarbons; "FOG" can refer to fats, oil and grease. Herein, depending on context, hydrocarbons can refer to relatively viscous hydrocarbons such as those (including mixtures) having a viscosity approximately at least similar to or greater than liquid kerosene at a similar temperature, particularly around room temperature, e.g. room temperature ±10° C.

Figure 7:
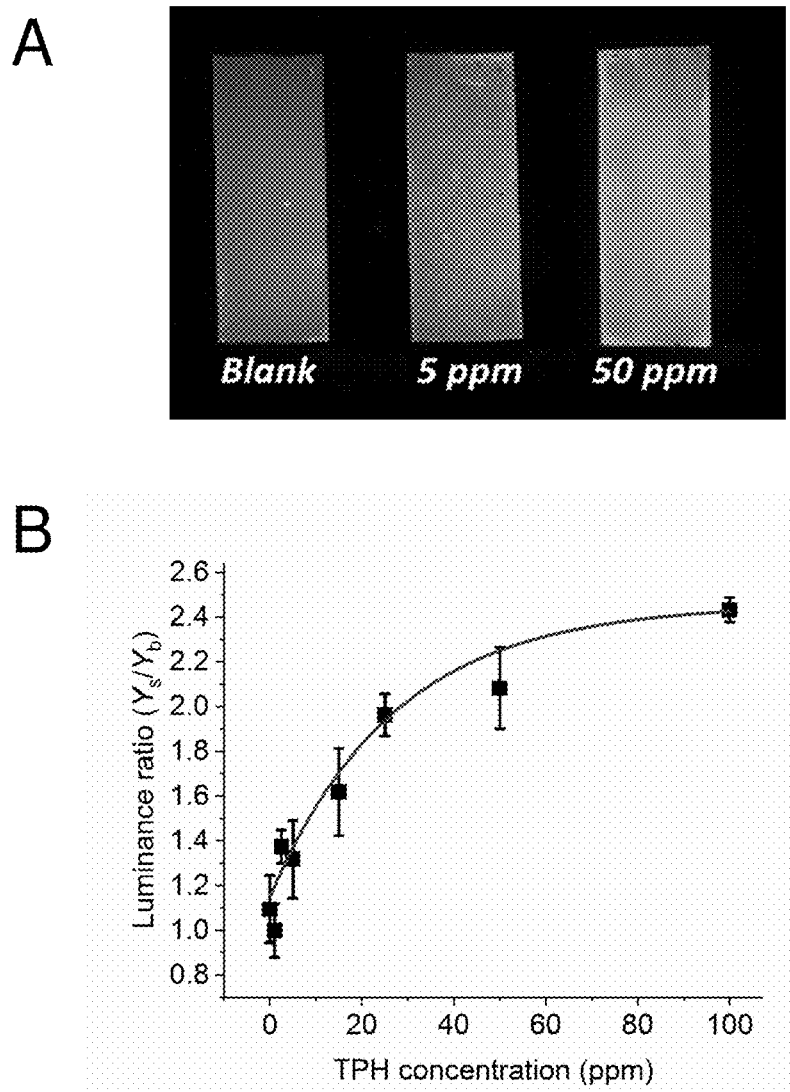
FIG. 7(A) shows photoluminescence from test strips which include immobilized molecular probes exposed to varying amounts of hydrocarbons, according to embodiments described herein.
FIG. 7(B) depicts photoluminescence from test strips which include immobilized molecular probes exposed to varying amounts of hydrocarbons, according to embodiments described herein.

FIG. 7(A) shows the photoluminescence of test strips exposed to 0 ppm, 5 ppm, and 50 ppm total petroleum hydrocarbon (TPH) in water, according to embodiments described herein. As illustrated in FIG. 7(A), a test strip that includes an immobilized photoluminescent molecular probe on a substrate can become more luminescent upon exposure to a sample of hydrocarbon contaminated water. FIG. 7(B) illustrates, according to embodiments described herein, photoluminescence collected from sample(s). FIG. 7(B) can illustrate a luminescence ratio versus TPH. To contact the sample with the molecular probe, one can immerse the test strip in the sample (e.g. a liquid sample, particularly aqueous, such as 250 ml of liquid sample) and shake. Subsequently, the test strip can be paper-dried, and the photoluminescence collected. It is also possible to extract the hydrocarbons using a volatile solvent, and contacting the extraction to the test strip.

Figure 5:
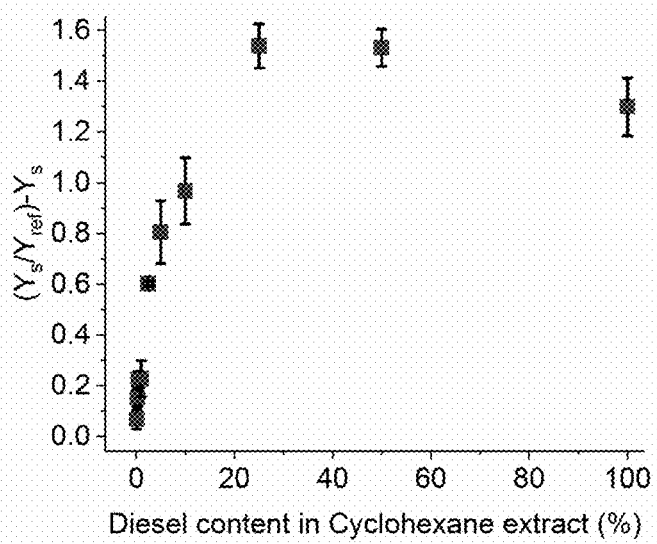
FIGS. 5(A) and 5(B) illustrate photoluminescence from immobilized molecular probes exposed to varying amounts of hydrocarbons, according to embodiments described herein.
Figure 5:
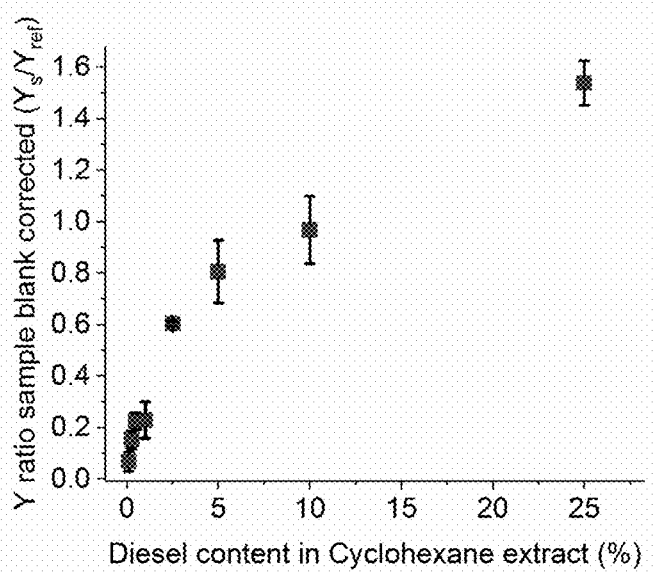

The collected photoluminescence can be compared to a reference such as a calibration, which may allow for quantitative determination of hydrocarbon contamination. FIG. 5(B) illustrates, according to embodiments described herein, a photoluminescence collected from molecular probe(s) that have been in contact with sample(s). For example, as shown in FIG. 5(B), a calibration can be used, such as one obtained by exposing the test strip to known concentrations of hydrocarbons, and collecting photoluminescence. The calibration can be in tabular and/or functional form, for example.

According to embodiments described herein, an extraction of a water sample can be done and the extraction can be contacted to the molecular probe. For example, the extraction solvent can be a light hydrocarbon such as cyclohexane and/or pentane, or the like. The volumes of the water sample and extraction solvent can be optionally predetermined/known. It can be possible to determine the hydrocarbon content in the water sample when the hydrocarbon content of the extract (which may be reduced in volume by evaporation or the like) is determined. It is possible to dilute samples, such as highly contaminated samples, or extracts of high hydrocarbon content, such as before contacting them with the molecular probe, which may increase accuracy.

Figure 1:
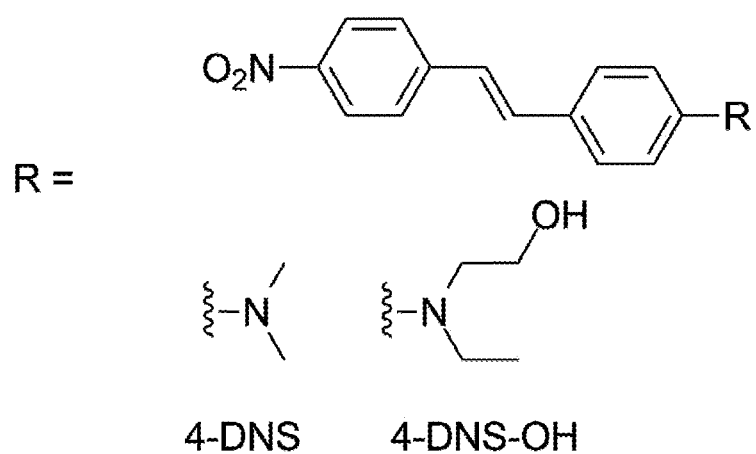
FIG. 1 depicts molecular probes, according to embodiments described herein.

FIG. 1 shows molecular probes, according to embodiments described herein. The photoluminescence properties of a molecular rotors DNS and DNS-OH (4-DNS-OH or 2-[ethyl[4-[2-(4-nitrophenyl)ethenyl]phenyl]amino]ethanol) can be particularly useful for detecting hydrocarbons in water. DNS and 4-DNS-OH can be regarded as a push-pull based stilbene exhibiting strong fluorescence emissions on highly viscous microenvironments. If viscosity decreases, molecular twisting in the excited state can allow access to a TICT (twisted intramolecular charge transfer) state, from which the molecular probe can deactivate via radiationless pathways. Without being bound by theory, when the 4-DNS-OH is in a free state, such as in a low viscosity environment, including possibly immobilized on a substrate without analyte, the molecular probe may have relatively low photoluminescence possibly due to the high degree of freedom. In the presence of PH, relatively high viscosity may hinder the molecular twisting, thus increasing photoluminescence.

According to embodiments described herein, the TICT state can be variably accessible, such as variably accessible depending on the presence of hydrocarbons. Viscous nonpolar hydrocarbons may particularly hinder the accessibility of a TICT state.

Figure 3:
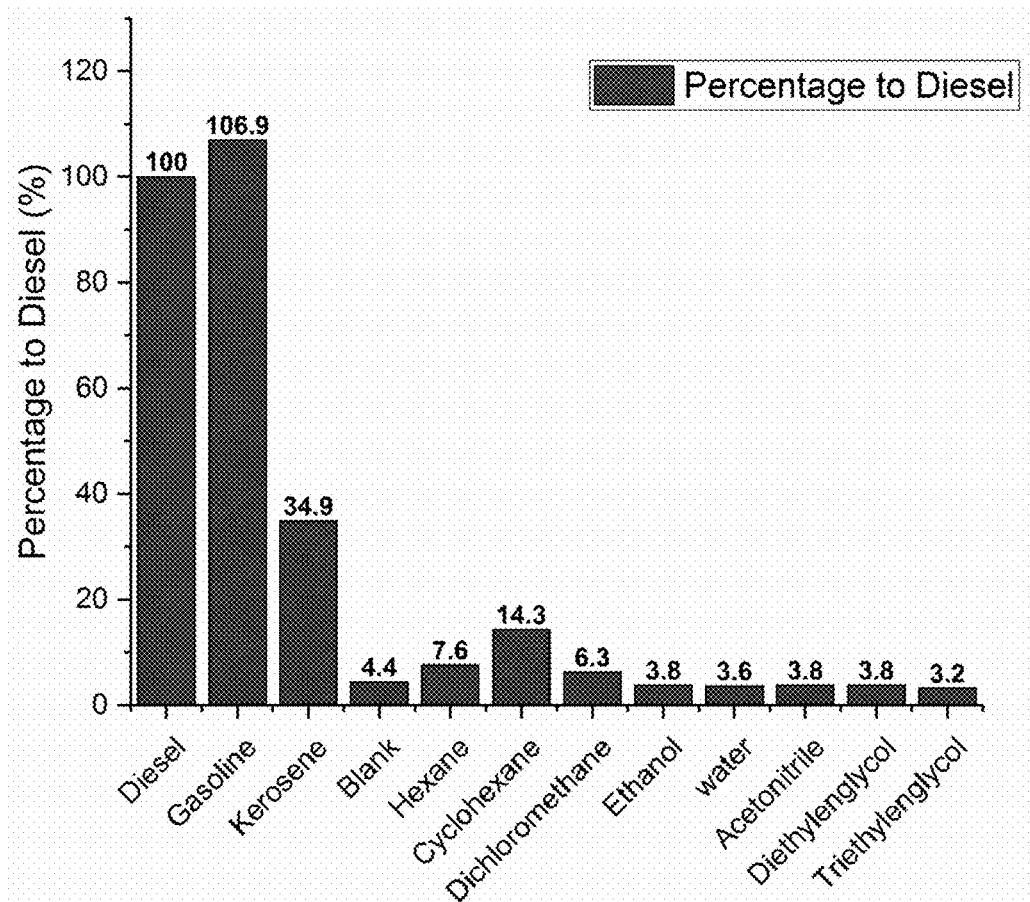
FIG. 3 illustrates photoluminescence from molecular probes exposed to varying liquids, according to embodiments described herein.

FIG. 3 shows, according to embodiments described herein, (normalized) photoluminescence of a molecular probe, such as, particularly, 4-DNS-OH test strips after dipping in various liquids, as a means to contact sample with the molecular probe. Photoluminescence of 4-DNS-OH may be increased in viscous nonpolar hydrocarbons. Other family members of DNS based molecular probes may display similar trends and also be suitable in the disclosed invention, which may exploit environmentally sensitive photoluminescence. Other molecular probes that have a variably accessible TICT state may also be suitable.

Without being bound by theory, hydrogen bonding interaction of polar solvents with the free electron pair of the amino group of 4-DNS-OH may favor a radiationless intramolecular charge transfer that inhibits the photoluminescence. For example, hydrogen bonding at the amino group can weaken the electron donating strength of that functional group, and may slow down the intramolecular charge transfer. This can weaken the fluorescence. Strong hydrogen bonds of N and/or O atoms of the molecular probe can also dissipate excitation energy via non-fluorescent vibrational pathways, thus possibly depriving the system of a possibility to relax by emission of a photon. Large amounts of water may inhibit fluorescence even if there is a large amount of oil analyte that is present. Therefore, according to an embodiment that may be combined with any other embodiment described herein, the molecular probe can be embedded in a substrate and/or immobilized to a substrate, such as a hydrophobic polymer. This may protect the molecular probe from polar solvent (e.g. water) interactions. It can also allow for the hydrocarbon of the sample to contact the molecular probe, such as by diffusion. Furthermore, the use of a substrate can confer the system a solid support to work with as a convenient test-strip. For example, polyvinylidene fluoride (PVDF) can be the hydrophobic substrate to which the molecular probe is immobilized. It may also be advantageous for the substrate to be porous. A porous PVDF substrate is particularly contemplated, e.g. to allow oil adsorption while having negligible interaction with water.

Table 1 shows maximum emission wavelengths and FEF (fluorescence enhancement factor) of 4-DNS-OH in solution when excited at 400 nm, according to embodiments described herein.

Figure 2:
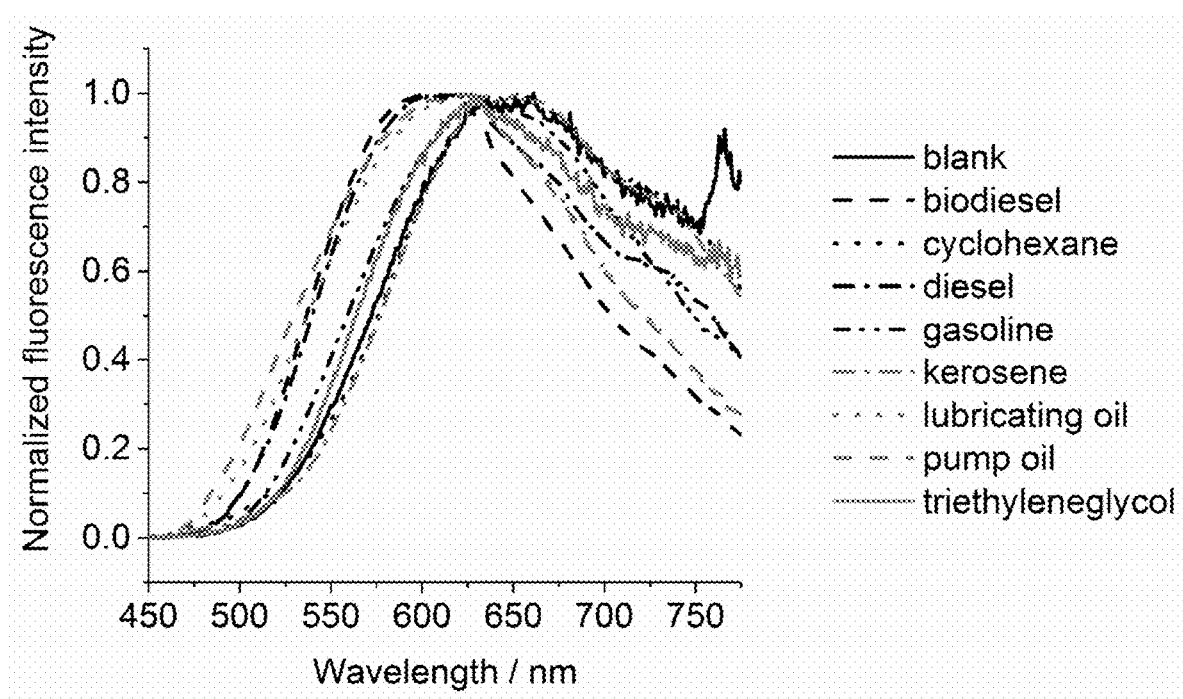
FIG. 2 depicts normalized fluorescence emission of an immobilized molecular probe wetted with different solvents, according to embodiments described herein.

FIG. 2 shows normalized fluorescence emission of 4-DNS-OH PVDF polymer, wetted with different solvents, according to embodiments described herein. Films of PVDF were dip coated with a toluene solution of 4-DNS-OH. After toluene evaporation, the films showed background fluorescence band at 657 nm. Different hydrocarbon aliquots were then added to this film and the emission spectra were recorded. As expected, the different hydrocarbons showed enhancements of the fluorescence bands as well as some bathochromic shifts, while other low weight hydrocarbons showed small signals, and polar liquids showed negligible changes.

To prepare the 4-DNS-OH immobilized PVDF, for example, 40×40 mm polivynilidene fluoride films (Amersham Hybond P0.2 PVDF) can be dip coated for 5 seconds in 4 mL 4-DNS-OH solution (e.g. $1 \times 10^{-3}$ M toluene) on a Petri dish. After taking the strip out of the solution, the excess of liquid can be absorbed in a paper from one of the film borders, and the toluene was allowed to evaporate while the film is suspended horizontally from its four corners.

Figure 4:
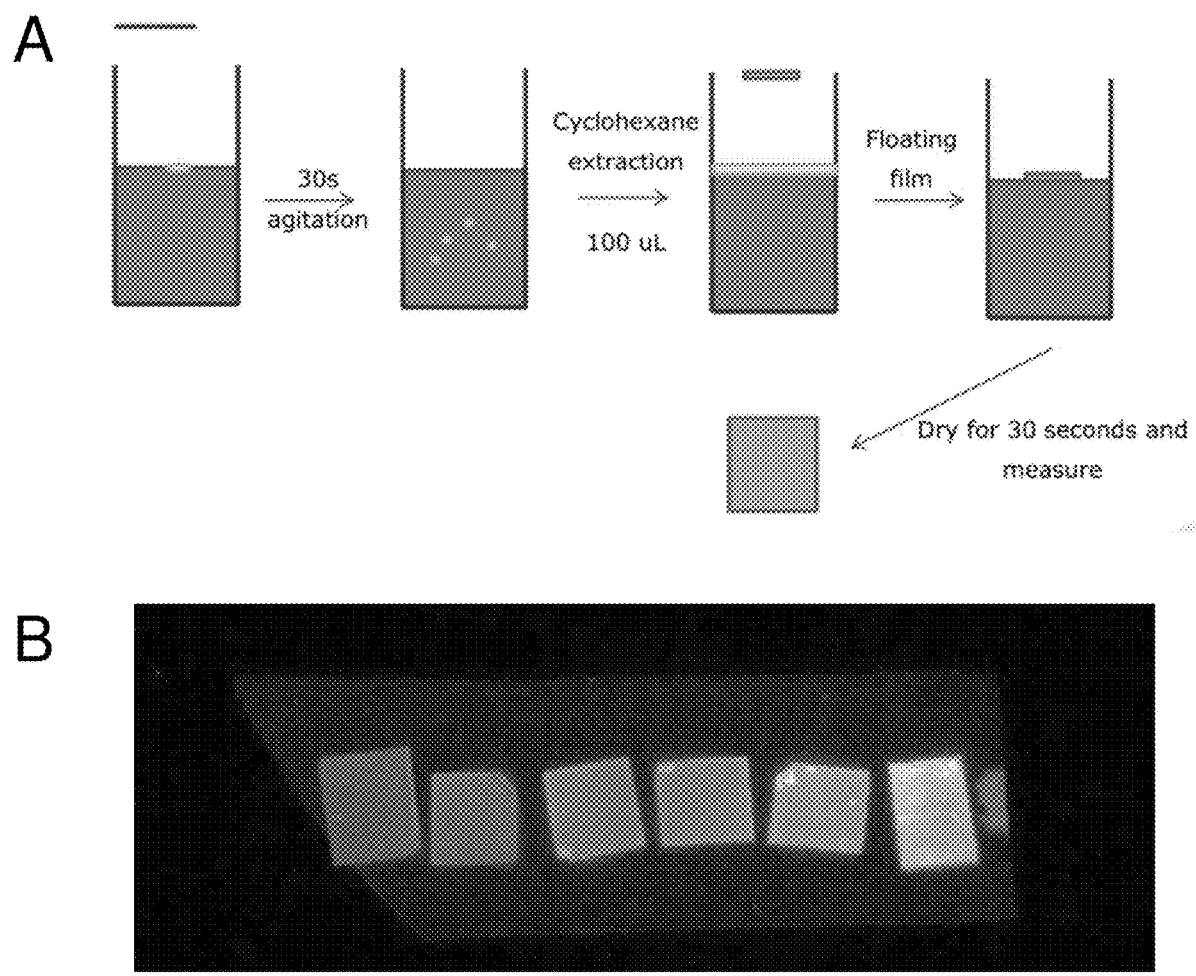
FIG. 4(A) shows, according to embodiments described herein, using a floating substrate to contact a sample with a molecular probe.
FIG. 4(B) illustrates photoluminescence from immobilized molecular probes exposed to varying amounts of hydrocarbons, according to embodiments described herein.

FIG. 4(B) is representative of photoluminescence from 4-DNS and/or 4-DNS-OH immobilized on PVDF, in the absence and presence of hydrocarbons, according to embodiments described herein. Under these immobilized conditions, the compound 4-DNS has an emission maximum at about 646 nm, and the emission from 4-DNS-OH has a maximum at 657 nm. It is possible to prepare the test strips by exposing the substrates for 3 seconds in 1 mM molecular probe solution in toluene, and allowing them to subsequently dry for 5 minutes, for example.

FIG. 4(A) shows, according to embodiments described herein, a way that the sample can be contacted with an immobilized molecular probe. According to embodiments described herein, the substrate can be floated on a sample, such as to absorb a hydrocarbon layer present at the air/liquid interface; the hydrocarbon layer can be an extraction of a mostly aqueous sample, for example. A portion of light hydrocarbon, such as cyclohexane, can be added to a sample, such as a water based sample; the mixture can be agitated, and allowed to settle; a substrate that includes the immobilized molecular probe can be floated on the surface of the mixture, removed, optionally dried, and the photoluminescence collected from the molecular probe immobilized/embedded on the substrate. By floating the substrate, the molecular probe can be contacted by the hydrocarbons extracted from an aqueous sample or the like.

FIG. 4(B) illustrates, according to embodiments described herein, immobilized photoluminescent molecular probes on substrates that have been exposed to varying concentrations of diesel fuel in water. Contact with greater concentration of diesel fuel can result in an increase of photoluminescence (e.g. left to right of FIG. 4(B)).

FIGS. 5(A) and 5(B) illustrates, according to embodiments described herein, a photoluminescence collected from molecular probes that have been in contact with sample(s). FIGS. 5(A) and 5(B) can illustrate, according to embodiments described herein, a photoluminescence that can be collected from immobilized molecular probes that have been contacted with varying levels of hydrocarbon contaminated sample, particularly diesel in water.

The examples of FIGS. 4(A), 4(B), 5(A), and 5(B) support that it is possible to have a limit of detection of approximately 0.6% diesel in cyclohexane when using 365 nm excitation with 4-DNS immobilized on PVDF. The examples also support using a "floating substrate" to contact the sample with the molecular probe.

Figure 8:
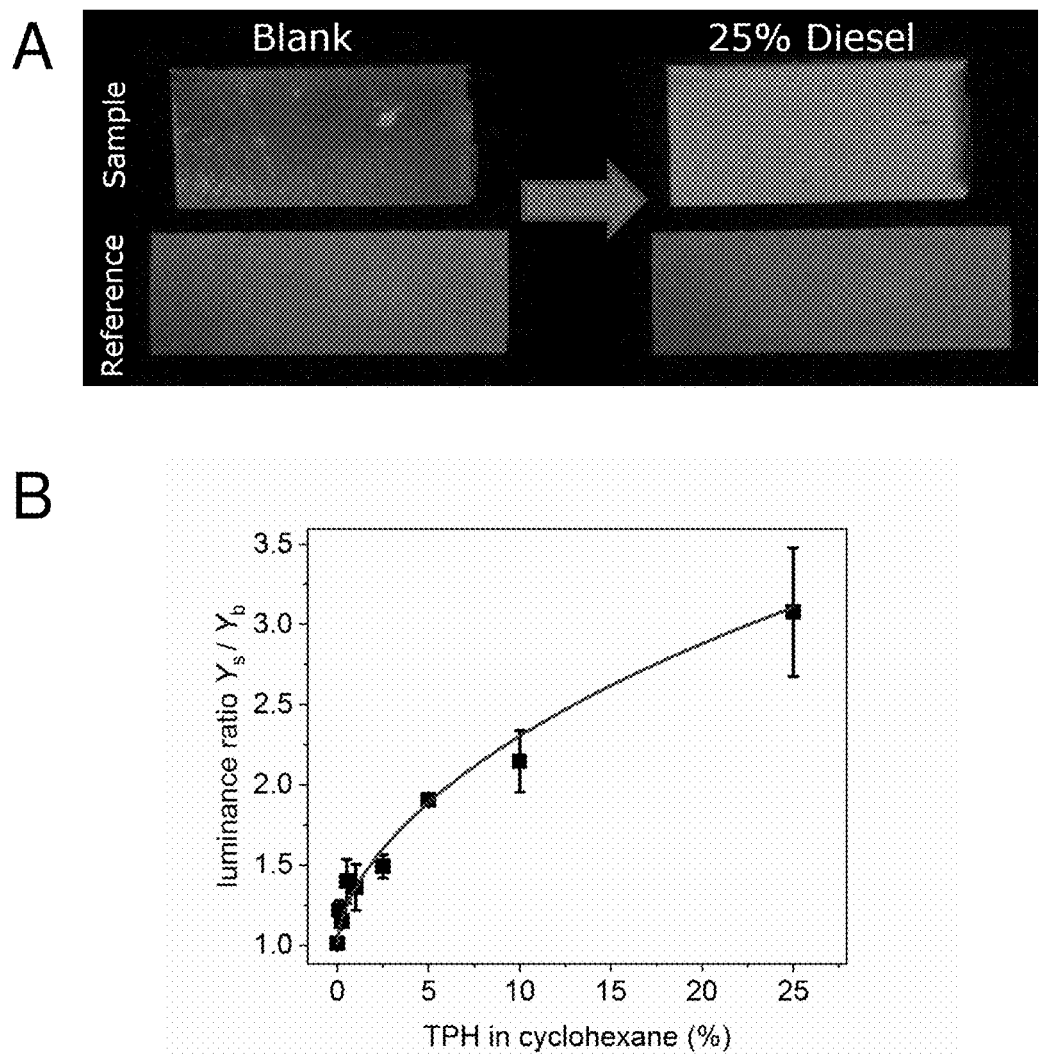
FIGS. 8(A) and 8(B) illustrate photoluminescence from immobilized molecular probes exposed to varying amounts of hydrocarbons, according to embodiments described herein.
Figure 9:
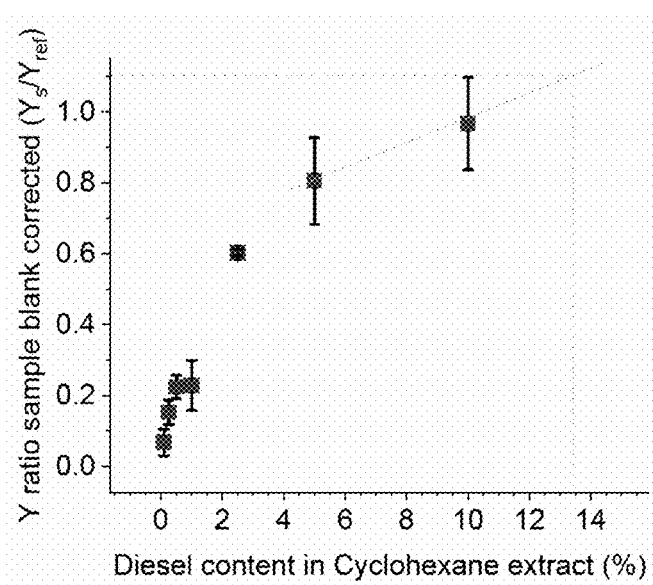
FIG. 9 illustrates photoluminescence from immobilized molecular probes exposed to varying amounts of hydrocarbons, according to embodiments described herein.

FIG. 8(A) illustrates, according to embodiments described herein, immobilized photoluminescent molecular probes on substrates for the detection of diesel. FIG. 8(A) shows an increase in luminance upon contact of the molecular probe with diesel, which can be diesel extracted from an aqueous sample.

FIGS. 5(A) and 5(B) illustrate, according to embodiments described herein, a photoluminescence collected from molecular probes that have been in contact with sample(s). FIGS. 5(A) and 5(B) can illustrate, according to embodiments described herein, an immobilized molecular probe used to detect diesel in water after extraction of the diesel by use of light hydrocarbons such as pentane and/or cyclohexane. It can be convenient to utilize extraction and to contact the extraction with the molecular probe rather than have a contaminated water sample directly contact the molecular probe. Such extractions can aid in quantitative determination of water contamination. FIGS. 5(A) and 5(B) illustrate, according to an embodiment, the photoluminescence signal of 4-DNS-OH immobilized to a substrate, with excitation at 460 nm using a 10 mW LED and 480 nm low pass filter (after exposure to various concentrations of diesel in cyclohexane). The photoluminescence can be collected through a 525/50 nm bandpass. From FIGS. 13 and 14, it is seen that low concentrations (e.g. 0-5%) of hydrocarbons may provide lower error, e.g. 0.2%, than higher concentration (e.g. 5-50%) which may provide higher error, e.g. 2.7%. In an embodiment, that may be combined with any other embodiment described herein, samples may be diluted so as to increase accuracy of a quantitative determination of hydrocarbon contamination. FIGS. 5(A) and 5(B) illustrate, according to embodiments described herein, that the method can be performed on liquid extractions of samples, such as extraction from water or soil.

For example, a reference such as a calibration curve can be generated, such as one illustrated by FIGS. 5(A) and 5(B)(B), for a hydrocarbon extracted from an aqueous sample, such as an extraction using a light hydrocarbon such as pentane and/or cyclohexane.

Alternatively/additionally, a sample may be a soil sample. For example, a molecular probe may be contacted with the sample by using a molecular probe immobilized on a substrate, and directly contacting a soil sample with the substrate. A test strip may be dragged, wiped, or swabbed across a soil sample.

Figure 10:
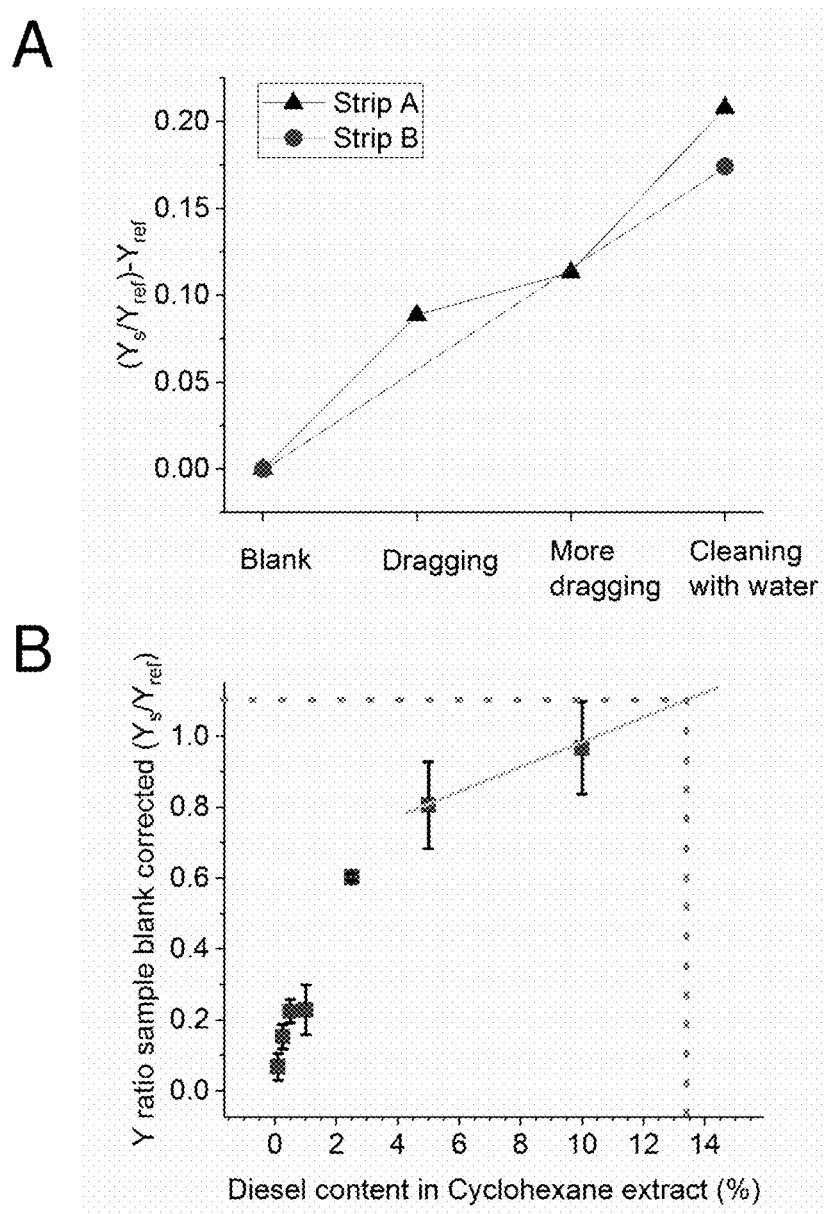
FIG. 10 illustrates photoluminescence from immobilized molecular probes exposed to varying amounts of hydrocarbons, according to embodiments described herein.

FIG. 10(B) illustrates, according to embodiments described herein, photoluminescence collected from molecular probes exposed to samples. FIG. 10(B) can illustrate the photoluminescence from test strips of immobilized molecular probes which have been in contact with samples prepared by pentane and/or cyclohexane extraction of hydrocarbon contaminated soil.

FIG. 10(A) illustrates, according to embodiments described herein, photoluminescence collected from molecular probes that have been in contact with samples. FIG. 10(A) can depict the photoluminescence from test strips of immobilized molecular probes which have been in contact with soil samples, such as direct contact. The test strip can be dragged, wiped, or swabbed across a soil sample and subsequently rinsed. The test strip can be in direct contact with the soil sample for 30-60 seconds and subsequently rinsed with water, such as to ensure soil particles are significantly removed the surface of the test strip. The photoluminescence can be a qualitative test for the presence of hydrocarbon contamination.

Figure 6:
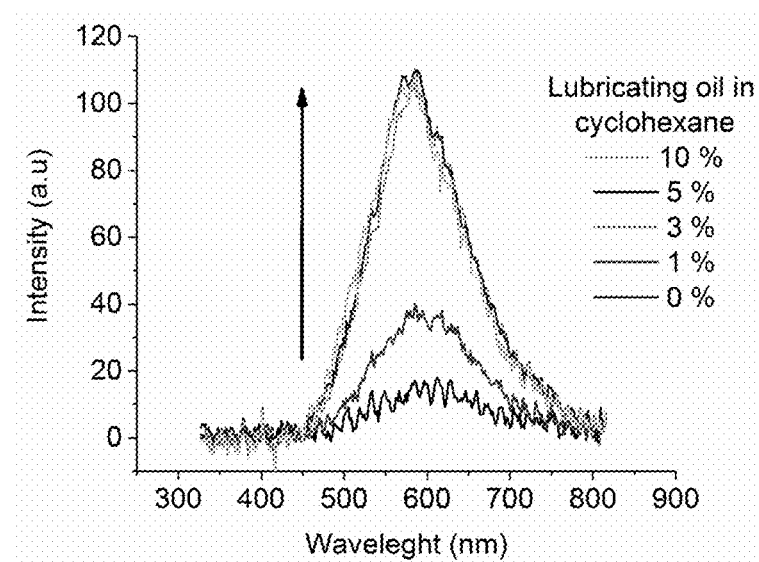
FIG. 6 illustrates photoluminescence of a molecular probe immobilized on a substrate upon exposure of increasing amounts of hydrocarbon, according to embodiments described herein.

FIG. 6 illustrates, according to embodiments described herein, a photoluminescence of a molecular probe after contact with a sample(s). For example, the sample can be a cyclohexane extraction of lubricating oil from a soil or water sample, which is contacted with a test strip. Alternatively/additionally, FIG. 6 can be representative of a reference such as a calibration.

FIG. 5(A) illustrates, according to embodiments described herein, a photoluminescence of a molecular probe after contact with a sample(s). Alternatively/additionally, FIG. 5(A) can be representative of a reference such as a calibration of a test strip. The test strip can have a dynamic range up to a concentration of hydrocarbon (e.g. lubricating oil) at which the immobilized molecular probe is saturated, such as up to 3%. The saturation concentration can depend, for example, on the time of contact of the test strip with the molecular probe, the size of the test strip, the test strip's capacity for adsorbing liquid, and the volume of sample.

According to embodiments described herein, it may be useful, upon collection of the photoluminescence, to measure integrated photoluminescence intensity for example, particularly within a spectral range of photoluminescence of the molecular probe, to determine whether there is a hydrocarbon contaminated sample.

Figure 11:
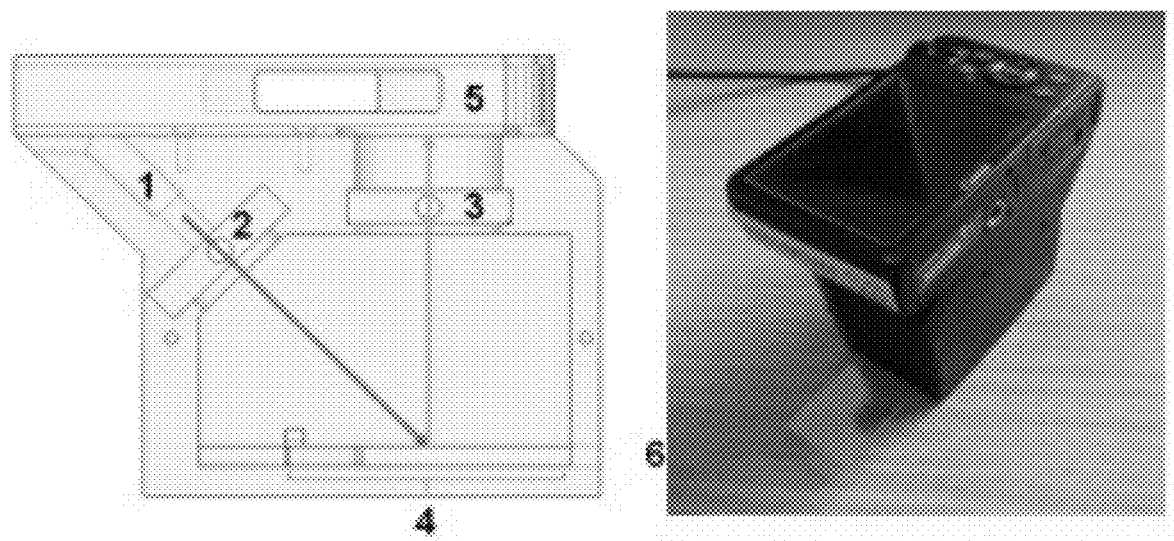
FIG. 11 depicts, according to embodiments described herein, a portable device for collecting the photoluminescence from molecular probes.

FIG. 11 illustrates, according to embodiments described herein, a portable electronic device for the detection of hydrocarbon contamination in a sample. A dark chamber can be used for reducing background signal. The device can include light source 1 such as an LED, a filter 2 such as a diffuser and/or short pass filter, such as a 460 nm short pass, for filtering the excitation light, a filter 3 for filtering the collected photoluminescence such as a 550 nm band pass filter, a test strip 4, and a portable device (such as a smartphone, tablet, digital camera, and/or mobile communication and computing device). The portable device can include a lens and camera, for example. The portable device can include a processor and memory for logic and data processing, such as for determining whether the photoluminescence is indicative of a hydrocarbon contaminated sample.

Further Details of Exemplary Embodiments

Some of the following may be duplicative of the above, as the above part of the description may have explained the invention more generally than or similarly to each of the possibly more specific experiments described below, which may have been performed to test and confirm some of the features and/or general principals of the invention.

Reference materials. Certified Reference Material BAM-U021 (BAM, Federal Institute for Materials Research and Testing, Berlin, Germany) was used for quantification of mineral oil in contaminated soil (TPH=3560±260 mg/Kg).

Kerosene was commercially available at Sigma Aldrich. Gasoline (E5 grade) and diesel were obtained from a HEM gas station (Berlin-Adlershof, January 2016). Biodiesel was obtained from the Center of Documentation, Research and Experimentation on Accidental Water Pollution (Cedre, Brest, France, June 2016).

Steady-state fluorescence measurements were carried out on a FluoroMax-4 spectrofluorometer from Horiba Jobin-Yvon, using standard 10 mm path length quartz cells when performing solution experiments, or in a front-face set-up at 60° when recording test-strips fluorescence. All the solvents employed for the spectroscopic measurements and interference assays were of UV spectroscopic grade (Sigma Aldrich).

Fluorescence signal of the test-strip was monitored in some cases using a custom-made setup combining an excitation LED source of 460 nm, filtered with a band-pass filter at 480 nm, with a fluorescence selector at 550/25 nm, or using a hand-held laboratory UV lamp ($\lambda_e m=365$ nm) in a closed cabinet without further filtering. Images were recorded using a SONY RX100 II digital camera, normally using F6.5, S1/5 and ISO1600. Finally, pictures were treated numerically to extract the luminance Y values of the emitted fluorescence.

Preparation of Test Strips.

40×40 mm polyvinylidene fluoride films (Amersham Hybond P0.2 PVDF) were dip coated during 5 seconds in 4 mL 4-DNS-OH solution ($1 \times 10^{-3}$ M toluene) on a Petri dish. After taking the strip out of the solution, the excess of liquid was absorbed in a paper from one of the film borders, and the toluene was allowed to evaporate while the film was suspended horizontally from its four corners. For characterization purposes, several strips (400 mg in total) were washed 3 times with 3 mL of dichlorometane to extract all 4-DNS-OH. After measuring the absorbance of the resulting solution, the amount of molecular probe was determined to be of 1.2 mg×cm$^2$.

After preparation of ca $1 \times 10^{-6}$ M solutions of 4-DNS-OH in different hydrocarbon mixtures and registering their fluorescence spectra ($\lambda_{exc}=400$ nm), there are observed strong fluorescence intensities in the region of 600-650 nm. Diesel, gasoline, kerosene, biodiesel, pump and lubricating oil, as well as other low weight alkanes such as cyclohexane were used. Fluorescence intensities can be related to viscosities of the solvents used. The emission intensity of 4-DNS-OH in viscous hydrocarbons (e.g. diesel, gasoline, kerosene, crude oil, biodiesel) is of several orders of magnitude when compared to lower weight alkanes. Additionally, small shifts in $\lambda_{em}^{max}$ can be observed.

Experiments were run to explore the photophysical properties of 4-DNS-OH when immobilized on/embedded in PVDF polymer. Films of PVDF were dip coated with a toluene solution of 4-DNS-OH. When toluene evaporated from the film, the films showed background fluorescence band at 657 nm. Different hydrocarbon aliquots were then added to this film and the emission spectra were recorded. The different hydrocarbons showed enhancements of the fluorescence bands as well as some bathochromic shifts, while other low weight hydrocarbons showed small signals, and polar liquids showed negligible changes. Results of these experiments are summarized in the following table.

| Liquid | Solution $\lambda_{em}$/nm | FEF |
|---|---|---|
| Blank | 645 | 1.0 |
| Diesel | 609 | 6.0 |
| Biodiesel | 603 | 9.8 |
| Gasoline | 640 | 7.6 |
| Kerosene | 652 | 5.8 |
| Lubricating oil | 615 | 7.7 |
| Pump oil | 613 | 11.1 |
| Cyclohexane | 649 | 3.8 |
| Triethyleneglycol | 630 | 0.8 |

Table 1 above. Maximum emission wavelengths and FEF (fluorescence enhancement factor) of 4-DNS-OH in solution.

Qualitative Assay in Contaminated Water

The method can exploit advantageously the capacity of the test strip to adsorb hydrocarbons without interacting with more polar substances, such as possibly utilizing a hydrophobic substrate to keep water from the environment of the molecular probe immobilized on/embedded in the substrate. Once hydrocarbons are adsorbed, such as to the substrate and/or in a porous substrate, they can possibly interact as freedom constrainers with the molecular probe. For example, the adsorbed hydrocarbon can hinder the molecular probe from accessing the twisted intramolecular charge transfer state.

It is possible that dipping of the strip into a test solution is used as the way to contact the molecular probe with the sample.

Dipping the strip only in the top liquid surface can produce higher signals due PH top-layer formation compared to immersing the strip in to the center of the solution. Immersing the strip in a bottled solution and vigorously shaking it can produce reproducible results. A test-strip, particularly a porous one, may efficiently collect the present hydrocarbons/oil. FIG. 7(A) is representative of a result, the test strip being illuminated with UV light in a UV cabinet. FIG. 1 can be illustrative of 4-DNS-OH test strips: (left) blank; (middle and right) after dipping test strips into drinking water contaminated with 5 ppm TPH and 50 ppm of TPH. FIG. 7(B) is representative of a plot of measured luminance ($Y_s$) vs concentration of TPH in drinking water.

A sample strip can be added to a water sample (e.g. 250 mL with 5 to 50 ppm of PH). The sample was shaken vigorously for one minute and then, after paper-drying the strip, the photoluminescence collected. Additionally/alternatively, the extraction using volatile solvents is an option, particularly for precise results.

Calibration Curve for Quantitative Analysis of PH in Water 1 mL stock solutions of PH were prepared in cyclohexane ranging from 0.1 to 25%. Then, two test strips (blank and reference, 5×15 mm), such as those depicted in FIG. 7(A), were measured in a custom chamber such as that depicted in FIG. 11. Next, 15 µL of PH stock solution was added to the strip, and after 30 s for allowing cyclohexane evaporation, both reference and sample strips were measured again. This procedure was repeated for different concentrations. Then, the blank and reference luminance ratio was subtracted to the sample and reference luminance ratio $(Y_s/Y_{ref})-Y_{ref}$, and the result plotted vs PH concentration, yielding a reference, such as a calibration curve. FIG. 5(B) is illustrative of a calibration curve.

An average error of 2.7% was observed along a high concentrated section of the curve (5-50%), while at lower concentrations (0-5%) the error was 0.2%, yielding limits of detection of 0.6%.

Without being bound by theory, at high enough PH concentrations, a test strip of a molecular probe immobilized on a PVDF film can become inhomogeneously transparent due to the excess of analyte, which can possibly reduce the light absorption efficiency. It is therefore sometimes beneficial to dilute the sample to get more precise readings. In the case of needing to measure highly contaminated samples, 1/10 or 1/100 v/v cyclohexane dilutions are particularly contemplated.

Quantitative Assay of Contaminated Water 50 mL of pentane were added to a 250 mL sample of contaminated water (TPH content=1 ppm). After shaking for 1 minute, the pentane was separated, evaporated, and a stock solution in cyclohexane was prepared. Then, 15 µL of this solution were added to 5×15 mm strips. The luminance of these strips was measured in comparison to a blank reference.

Qualitative Assay in Soil

A contaminated soil sample (TPH content=3,250 ppm) was obtained. It was found that after putting 1 gram of soil in a petri dish, and rubbing a sensing strip over the soil for 1 minute, the fluorescence increased (as observed visually under blue light). The test-strip may be washed with water and gently rubbed with absorbing paper to eliminate soil particles prior to the measurement.

The molecular probe immobilized test strips can overcome many technical problems, allowing concentration of TPH in water to be quickly determined on-field, with the use of inexpensive technology (e.g. smartphone or tablet or digital camera) in both a qualitative (quickly dipping the strip in water and measuring it afterwards, without TPH extraction) and quantitative fashion (assisted with environmentally friendly solvents like cyclohexane).

Stability of the Films.

During the course of the experiments, there is observed negligible degradation of the test strip when treating it with PH. Without being bound by theory, the polar nature of the 2-ethanol moiety of 4-DNS-OH may help to keep low solubility of the molecular probe in the analyte liquids. Without being bound by theory, this may ensure low leaching. No bleaching was observed either when strip was kept under daylight, and the PVDF can be thermostable so as to lead to negligible degradation of the polymer films. Nevertheless, it is conceivable that, due to the absorbent nature of the polymer, after one analysis, the test strip can be disposed.

According to embodiments described herein, a polymeric strip containing a 4-DNS-OH molecular probe that becomes fluorescent in the presence of TPH is disclosed. This fluorescence is proportional to the amount of TPH in the sample. A disclosed system, according to embodiments described herein, is a test strip based system which simplifies the problem of detection TPH, TOG and FOG in water, making it possible to do on-field analysis of waters in oceans, lakes, rivers and water streams coming in and out of industries, as well as soil. Other laboratory based methods may require sampling, shipment to the laboratory and subsequent analysis. Thus, the disclosed invention saves time and cost.

The present invention has been explained with reference to various illustrative embodiments and examples. These embodiments and examples are not intended to restrict the scope of the invention, which is defined by the claims and their equivalents. As is apparent to one skilled in the art, the embodiments described herein can be implemented in various ways without departing from the scope of what is invented. Various features, aspects, and functions described in the embodiments can be combined with other embodiments.

The invention claimed is:

1. A method for the detection of hydrocarbon contamination in a sample, the method comprising:
contacting a sample with a molecular probe, the molecular probe having a photoluminescence; wherein the molecular probe is sensitive to viscosity and/or polarity of the sample;
collecting the photoluminescence from the molecular probe;
determining whether the photoluminescence is indicative of a hydrocarbon contaminated sample, wherein the molecular probe comprises a 4-nitrostilbene moiety according to the formula

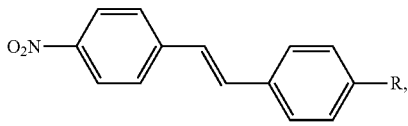

wherein R is selected from

referred to as 4-DNS,

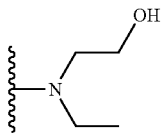 [SMILES: *N(CC)CCO]

referred to as 4-DNS-OH, and
an —N—R'R" moiety functionalized with a member selected from the group of: an alkyl, an alkenyl, an alkynyl, an alkyl halides, a thioalkyl, a hydroxyalkyl, an alkyl phosphate, an alkyl phosphoric, an alkyl boronate, an alkyl boronic, a carboxylic acid, a carboxylate, a sulfonic acid, a sulfonate, a silano, and combinations thereof.

2. The method of claim 1, wherein the molecular probe has a twisted intramolecular charge transfer state, the twisted intramolecular charge transfer state inducing less photoluminescence than another state.

3. The method of claim 1, wherein the molecular probe is a molecular rotor.

4. The method according to claim 1, wherein the molecular probe is solvatochromic and/or solvatokinetic.

5. The method of claim 1, wherein the molecular probe is immobilized on a hydrophobic substrate suitable for adsorbing 4-DNS-OH.

6. The method of claim 1, wherein the sample is water, soil, or an extract thereof.

7. The method of claim 1, further comprising
estimating a hydrocarbon content of the sample based on the photoluminescence.

8. The method of claim 1, wherein the sample is contacted to the molecular probe by dipping the substrate into the sample or dropping the sample onto the substrate or spraying the substrate with the sample.

9. The method of claim 1, further comprising
determining a signal, a brightness, a brightness ratio, a luminance, a photoluminescence quantum yield, a spectrum, and/or a photoluminescence kinetics; the determination being of the molecular probe in contact or after contact with the sample.

10. The method of claim 1, wherein a portable device collects the photoluminescence and determines whether the photoluminescence is indicative of the hydrocarbon contamination; the portable device comprising a lens and/or a fiberoptic for collecting the photoluminescence.

11. The method of claim 1, further comprising exciting the molecular probe with an ultraviolet or visible light source.

12. The method of claim 1, further comprising comparing the photoluminescence to a calibration.

* * * * *